United States Patent
Mastro et al.

(10) Patent No.: US 7,068,027 B1
(45) Date of Patent: Jun. 27, 2006

(54) SYSTEM FOR MEASUREMENT OF METALLIC DEBRIS IN FLUID

(75) Inventors: Stephen A. Mastro, Glen Mills, PA (US); John K. Overby, Nottingham, PA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 5 days.

(21) Appl. No.: 10/826,793

(22) Filed: Apr. 16, 2004

(51) Int. Cl.
*G01N 27/74* (2006.01)

(52) U.S. Cl. .................................... 324/204

(58) Field of Classification Search ................ 324/204; 73/53.05, 53.07, 61.41–61.42
See application file for complete search history.

(56) References Cited

U.S. PATENT DOCUMENTS

| | | | | |
|---|---|---|---|---|
| 3,553,672 A | * | 1/1971 | Smith | .................. 340/627 |
| 6,255,954 B1 | * | 7/2001 | Brown et al. | ................ 340/603 |
| 6,435,013 B1 | * | 8/2002 | Rodriguez et al. | ......... 73/61.75 |
| 2005/0002030 A1 | * | 1/2005 | Kolp et al. | .................. 356/335 |

OTHER PUBLICATIONS

Mehregany M. and Roy S., "Introduction to MEMS" from www.aero.org/publications, 10 pages.

* cited by examiner

*Primary Examiner*—Bot LeDynh
(74) *Attorney, Agent, or Firm*—Jacob Shuster

(57) ABSTRACT

A debris sensor arrangement is positioned within an enclosed body of fluid for detecting the presence of metallic debris particles therein. Debris detection involves exposure of cantilever beams to the fluid when magnetized within an electromagnetic field to attract the metallic debris particles thereon and induce vibratory motion thereof at a resonant frequency varied by changes in the density of the debris particles magnetically held thereon. Measurement of the resonance frequency reflecting the density of the debris particles within the fluid being tested thereby monitors the corresponding wear of machinery reflected by the debris density.

5 Claims, 2 Drawing Sheets

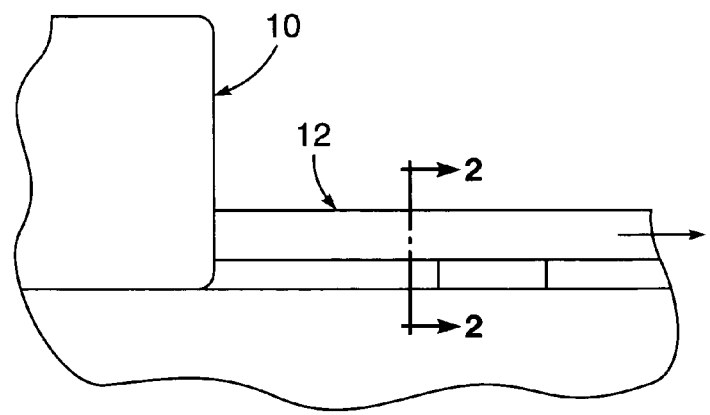
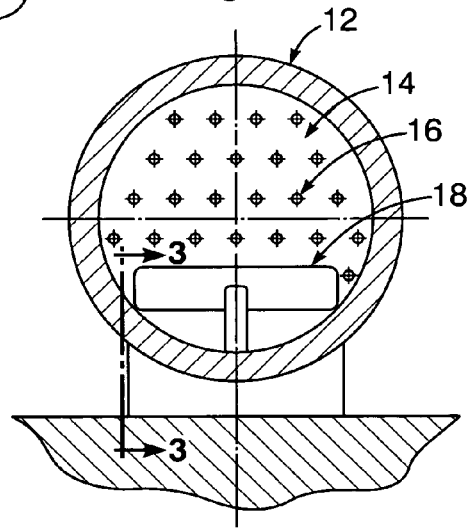
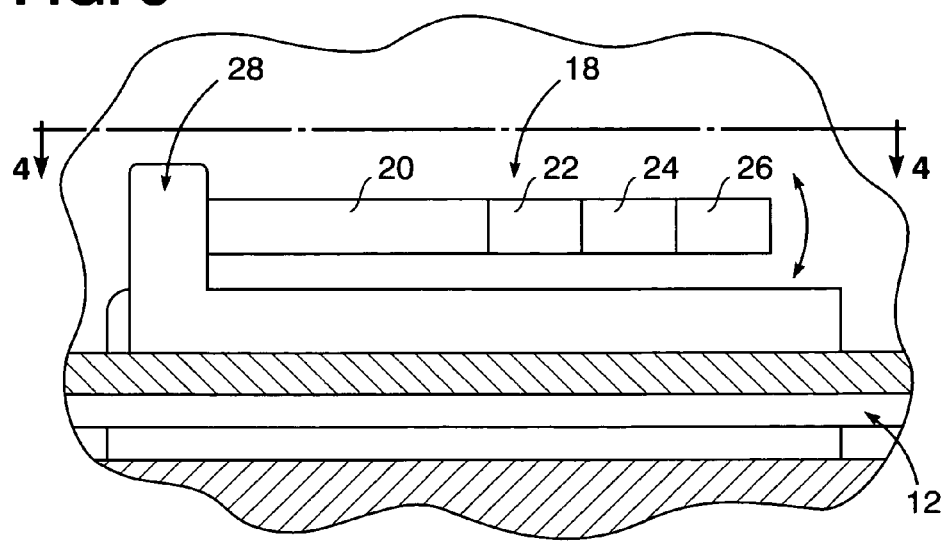

SYSTEM FOR MEASUREMENT OF METALLIC DEBRIS IN FLUID

STATEMENT OF GOVERNMENT INTEREST

The invention described herein may be manufactured and used by or for the Government of the United States of America for governmental purposes without the payment of any royalties thereon or therefore.

The present invention relates generally to debris detection and measurement in indicate associated mechanical parameters such as machinery wear.

BACKGROUND OF THE INVENTION

Currently measurement of machinery wear by detection of wear debris involves removal of oil samples from the machinery for analysis by use of magnetic Hall effect sensors, which may be intrusive and./or very expensive, where fiber optics types of such sensors are utilized. Other generally known optical fiber systems for monitoring metallic debris require algorithms to discern the metallic debris from air bubbles and other anomalies. It is an important object of the present invention to provide a relatively smaller and less intrusive system for the detection and measurement of metallic debris reflecting machinery wear.

SUMMARY OF THE INVENTION

Pursuant to the present invention, metallic debris is detected and measured directly within fluid enclosure while the fluid is undergoing flow therein from machinery for example. Magnetic attraction of particles of the metallic debris within such fluid onto cantilever beams of a generally known type associated with micro-mechanical systems is involved. The cantilever beams are positioned so that vibratory motion thereof is induced by electromechanical forces applied through a magnetic field which also establishes the magnetic attraction of the metallic debris onto the cantilever beams while the fluid is undergoing flow and monitors changes in resonance frequency of the vibratory motions reflecting variations in debris density within the fluid being tested reflecting wear of the machinery.

BRIEF DESCRIPTION OF THE DRAWING

A more complete appreciation of the invention and many of its attendant advantages will be readily appreciated as the same becomes better understood by reference to the following detailed description when considered in connection with the accompanying drawing wherein:

FIG. 1 is a partial side elevation view of a fluid flow line installation within which a micro electromechanical debris sensing system is positioned in an arrangement pursuant to one embodiment of the present invention;

FIG. 2 is a partial transverse section view taken substantially through a plane indicated by section line 2—2 in FIG. 1;

FIG. 3 is a partial section view taken substantially through a plane indicated by section line 3—3 in FIG. 2;

DETAILED DESCRIPTION OF THE PREFERRED EMBODIMENT

Figure 4:
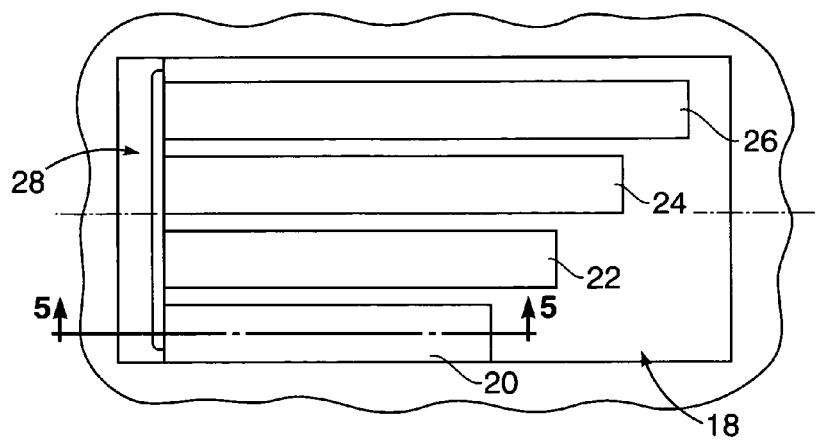
FIG. 4 is a partial top installational section view taken substantially through a plane indicated by section line 4—4 in FIG. 3.
Figure 5:
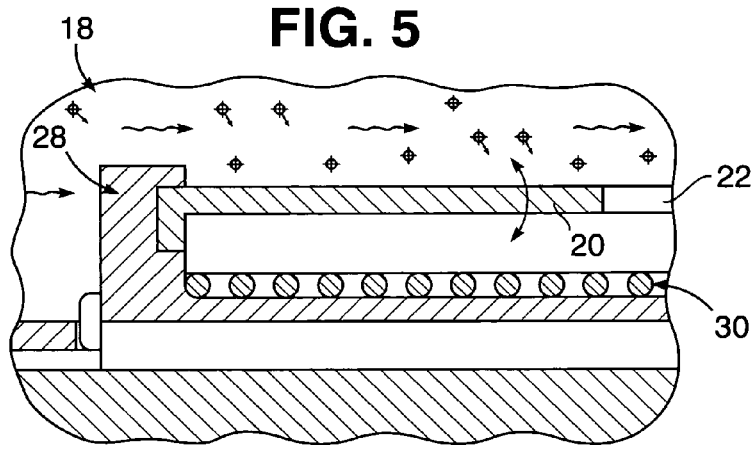
FIG. 5 is a partial section view taken substantially through a plane indicated by section line 5—5 in FIG. 4.

Referring now to the drawing in detail, pursuant to one embodiment of the present invention wear of machinery 10 for example is monitored by detection of debris within fluid enclosure such as a pipe 12 as shown in FIG. 1. Fluid 14 as shown in FIG. 2, such as non-turbulent water or lubricating oil, is to be tested for the presence of metallic debris therein, such as suspended non-magnetic particles 16 imparting a relatively low viscosity to the fluid 14 so as to enable detection of the debris particles 16 by a micro-mechanical type of sensor arrangement 18.

Figure 6:
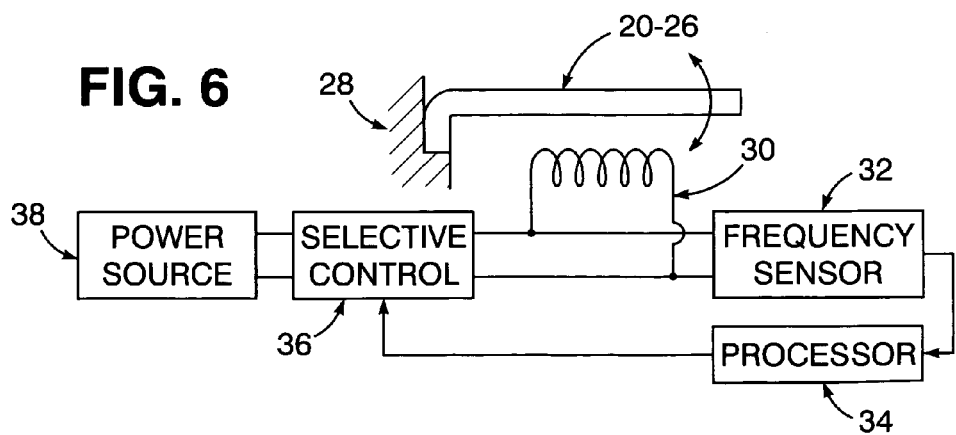
FIG. 6 is a diagram illustrating the electrical control system associated with the apparatus illustrated in FIGS. 1–5.

Referring now to FIGS. 2–5, the debris sensor arrangement 18 embodies a plurality of vibratory cantilever beams 20, 22, 24 and 26 of different lengths anchored at one end thereof within the pipe 12 by a support 28 in overlying relation to electromagnetic coils 30. The cantilever beams 20, 22, 24 and 26 undergo vibratory motion when rendered magnetic within an electromagnetic field generated by the underlying electromagnetic coils 30, upon electrical energization thereof as hereinafter explained. Under the electromagnetic forces thereby exerted on the cantilever beams 20–26 by the electromagnetic coils 30, their vibratory motions resonate at a resonance frequency dependent on their mass and the quantity of the metallic debris particles 16 deposited thereon by magnetic attraction. Because of such magnetic adherence of the metallic debris particles 16 onto the cantilever beams 20–26, changes in resonant frequency is detected by a resonance frequency sensor 32 diagrammed in FIG. 6, of a standard microbeam electronics type. The frequency sensor 32 is operationally connected to a data process indicator 34 to monitor debris density of the particles 16 in the fluid 14. A selective control 36 is connected to the data process indicator 34 for controlling supply of electrical energy from a power source 38 to the magnetic field coils 30 in accordance with the debris density being monitored.

The debris sensor arrangement 18 as hereinbefore described is utilized to detect the density of the metallic debris particles 16 within the body of fluid 14 being tested while undergoing flow within the pipe 12. The pipe 12 may constitute a lubrication line extending from the machinery 10 through which machinery wear is reflected by change in cantilever vibratory motion frequency detected by the sensor 32 for monitoring machinery wear reflected by debris density through the data process indicator 34 and to control changes in energization of the magnetic coil 30 through the selective control 36. According to other embodiments of the present invention, the debris sensor arrangement 18 may alternatively be located in other installation enclosures such as a debris storage tank associated for example with food or drug manufacturing or water purification systems for indication of use or wear therein by monitoring of debris density.

Obviously, other modifications and variations of the present invention may be possible in light of the foregoing teachings. It is therefore to be understood that within the scope of the appended claims the invention may be practiced otherwise than as specifically described.

What is claimed is:

1. A micro electromechanical system for indicating the presence of metallic debris particles within a body of fluid, comprising: sensor means positioned within an enclosure containing said body fluid for detection of the metallic debris particles in response to selectively controlled supply of energy thereto; and indicator means connected to the sensor means for monitoring density measurements of the debris particles detected within the body of fluid; said sensor means comprising: cantilever means mounted within the body of fluid for undergoing vibratory motion therein; electrically powered means establishing an electromagnetic field within the body of fluid in underlying relation to the cantilever means for inducing said vibratory motion and magnetically attracting the metallic debris particles thereto causing changes in resonant frequency of the vibratory motion reflected by said density measurements.

2. The system as defined in claim 1, wherein said body of fluid is undergoing flow in surrounding relation to the sensor means within the enclosure, with the metallic debris particles suspended within the body of fluid.

3. A micro electromechanical system for indicating the presence of metallic debris particles within a body of fluid, comprising: a pipe forming an enclosure through which said body of fluid undergoes flow; sensor means positioned within said enclosure containing said body of fluid for detection of the metallic debris particles in response to selectively controlled supply of electrical energy thereto; and indicator means connected to the sensor means for monitoring density measurements of the debris particles in response to said detection thereof within the body of fluid; said sensor means comprising: cantilever means mounted within the pipe for undergoing vibratory motion; electrically powered means establishing an electromagnetic field within the body of fluid in underlying relation to the cantilever means for inducing said vibratory motion and magnetically attracting the metallic debris particles thereto causing changes in resonant frequency of the vibratory motion reflected by said density measurements.

4. The system as defined in claim 3, wherein said cantilever means comprises: a support on which the electrically powered means is positioned within the pipe; and a plurality of cantilever beams of different lengths anchored to the support in overlying relation to the electrically powered means.

5. The system as defined in claim 4, wherein the electrically powered means comprises: magnetic coils.

* * * * *